United States Patent [19]
Wu et al.

[11] Patent Number: 5,723,486
[45] Date of Patent: Mar. 3, 1998

[54] 1,3 DITHIOLO(4,5)-1,3-DITHIOLO-2-THIONE DERIVATIVES, COMPOSITIONS AND USE AS ANTIMICROBIAL AND MARINE ANTIFOULING AGENTS

[75] Inventors: Weishi W. Wu; Duane R. Romer; Ravi B. Shankar; R. Garth Pews, all of Midland, Mich.

[73] Assignee: The Dow Chemical Company, Midland, Mich.

[21] Appl. No.: 678,026

[22] Filed: Jul. 10, 1996

[51] Int. Cl.$^6$ .......................... A01N 13/28; C07D 341/00
[52] U.S. Cl. ................................. 514/139; 549/33
[58] Field of Search ................... 549/33; 514/439

[56] References Cited

PUBLICATIONS

J. Chem. Soc. Perkin Trans. 1, Thomas K. Hansen et al., pp. 2873–2875, 1991.
J. Chem. Soc., Chem. Commun., Aravinda M. Kini et al., pp. 335–336, 1987.
Abashev et al., Zh. Org. Zhim., vol. 31, No. 11, pp.1705–1710, 1995.

Primary Examiner—José G. Dees
Assistant Examiner—Mary C. Cebulak
Attorney, Agent, or Firm—S. Preston Jones; James M. Pelton

[57] ABSTRACT

Disclosed are 1,3-dithiolo(4,5-d)-1,3-dithiino-2-thione compounds corresponding to one of the formulae:

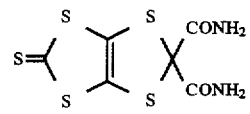

or

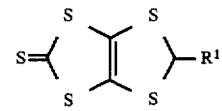

wherein $R^1$ represents —Br, —Cl, —F, —CN or —CH$(CH_2)_n$CH$_3$ and n is an integer of from 0 to 10.

These compounds as well as the unsubstituted compound have been found to exhibit antimicrobial and marine antifouling activity in industrial and commercial applications and compositions containing these compounds are so employed.

20 Claims, No Drawings

1,3 DITHIOLO(4,5)-1,3-DITHIOLO-2-THIONE DERIVATIVES, COMPOSITIONS AND USE AS ANTIMICROBIAL AND MARINE ANTIFOULING AGENTS

FIELD OF THE INVENTION

The present invention is directed to 1,3-dithiolo(4,5)-1,3-dithiole-2-thione compounds, compositions containing them and their use as antimicrobial and marine antifouling agents.

BACKGROUND OF THE INVENTION

Various 2-thione compounds are known. For example 1,3,4,6-tetrathiapentalene-2-thione having the formula

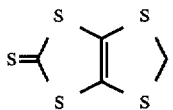

is taught by Hansen et al. in *J. Chem. Soc.*, Perkins Trans. 1, 1991, pages 2873–2875, especially page 2874. This compound is useful in preparing other thione compounds which may have superconducting properties. This compound is also taught by Kiki et al. in *J. Chem. Soc. Chem. Commun.*, 1987, pages 335–336 where it is taught as an intermediate.

SUMMARY OF THE INVENTION

The present invention is directed to 1,3-dithiolo(4,5)-1,3-dithiole-2-thione compounds corresponding to one of the formulae:

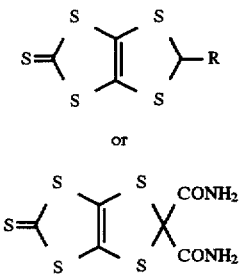

wherein R represents —H, —Br, —Cl, —F or —CN.

The present invention is also directed to antimicrobial compositions comprising an inert diluent in admixture with an antimicrobially-effective amount of a 1,3-dithiolo(4,5)-1,3-dithiole-2-thione compound corresponding to one of the formulae:

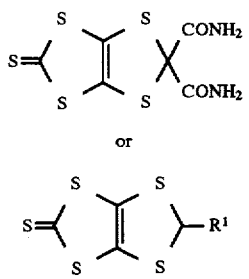

wherein $R^1$ represents —H, —Br, —Cl, —F, —CN or —CH$_2$(CH$_2$)$_n$CH$_3$ and n is an integer of from 0 to 10.

The present invention is further directed to a method for inhibiting microorganisms in a microbial habitat comprising contacting said microbial habitat with a composition containing an antimicrobially-effective amount of a compound corresponding to Formulae 1b and 1c.

The antimicrobial compositions of the present invention can also be employed to treat surfaces exposed to a marine environment in which marine organisms grow to prevent the growth of said marine organisms on said surfaces.

The preferred compounds of the present invention which are used in the antimicrobial compositions include those of Formulae 1b and 1c and especially those of Formula 1c, wherein $R^1$ represents —CH$_2$(CH$_2$)$_n$CH$_3$ and n is 10.

DETAILED DESCRIPTION OF THE INVENTION

The 1,3-dithiolo(4,5-d)-1,3-dithole-2-thione compounds of the present invention can be prepared by reacting, with agitation and in a polar solvent, a 4,5-dimercapto-1,3-dithiole-2-thione alkali metal salt corresponding to the formula

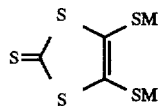

wherein M represents sodium, potassium or lithium, with an appropriate halide reactant corresponding to the formula C(X)$_2$RR$^1$ wherein X is chloro, bromo or iodo and R and $R^1$ are as hereinbefore defined.

Representative polar solvents which can be employed in the present process include water, dimethylformamide, dimethylsulfoxide and acetone.

The reactions are typically carried out at room temperature under a nitrogen atmosphere. The reactants may be added to the reaction mixture in any order of addition; conventionally they are added as a solution in the solvent used for the reaction. The reaction is allowed to continue over a period of from about ten minutes to about 15 hours. The reaction consumes the reactants in the ratio of one mole equivalent of the halide reactant per mole of the thione reactant. To insure the completion of the reaction, an excess of the halide reactant is normally employed.

After the reaction is complete, the product normally precipitates out and is recovered by filtration. To insure product precipitation, a slight amount of water and/or methanol can be added to the reaction mixture. The recovered product is washed with water or methanol and dried.

The following examples illustrate the present invention and the manner by which it can be practiced but, as such, should not be construed as limitations upon the overall scope of the same.

Since the hereinabove and hereinafter set forth compound preparation procedures employ only standard chemistry practices and it is known that slightly different reactants can require slightly different reaction parameters from those of other reactants, it is to be understood that minor modifications to the reaction parameters set forth such as the use of an excess of one reactant, the use of a catalyst, the use of temperatures slightly higher than room temperature and/or high speed mixing and other such conventional changes are within the scope of the present invention.

The structure identity of all compounds is confirmed by proton nuclear magnetic resonance spectroscopy ($^1$H NMR), recorded at 300 MHz; carbon nuclear magnetic resonance spectroscopy ($^{13}$C NMR) recorded at 75 MHz; infrared spectroscopy (IR) and mass spectrometry (MS). All of the reactions are conducted under a positive pressure of nitrogen.

EXAMPLE I 1,3-Dithiolo(4,5-d)-1,3-dithiole-2-thione

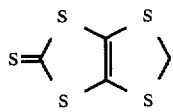

This compound is taught in the art as set forth hereinbefore. It may be prepared as follows:

Method 1

A mixture of 6.25 grams(g) (8.7 mmol) of bis(tetraethylammonium)bis-(2-thioxo-1,3-dithiole-4,5-dithiolate) Zn(II) and 33 mL of dibromomethane in 300 mL of acetone was reacted at room temperature for 3 days. The reaction mixture was filtered to get a first crop of 2.4 g of the title compound as a brown powder. The acetone was evaporated and the residual solid was washed with water to give 1.1 g of the title compound as a dark brown powder which melted at 150° C. (dec) in a yield of 95 percent based on the zinc reactant. MS (EI) m/z 210 (M$^+$), 166, 146, 134, $C_4H_2S_5$ requires 210; $^1$H NMR (DMSO-$d_6$)δ5.15(2H, s, $CH_2$).

Method 2

A mixture of 1.15 g (2.8 mmol) of sodium dithiolate and 33 mL of dibromomethane in 15 mL of dry DMF was reacted at room temperature for 4 hours. The reaction mixture was filtered to give 0.45 g of the title compound as a brown powder in a yield of 77 percent of theoretical. The analytical results were consistent with the data obtained above in Method 1.

EXAMPLE II

5-Chloro-1,3-Dithiolo(4,5-d)-1,3-dithiole-2-thione

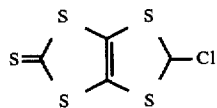

A mixture of 1.15 g (2.8 mmol) of sodium dithiolate and 0.58 g (2.8 mmol) of dibromochloromethane in 15 mL of dry DMF was reacted at room temperature for 8 hours. The reaction mixture was filtered to give 0.36 g of the title compound as a dark brown powder which melted at 120° C. (dec) in a yield of 53 percent of theoretical.

EXAMPLE III

5-Cyano-1,3-Dithiolo(4,5-d)-1,3-dithiole-2-thione

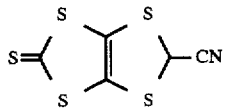

A reaction mixture of 1.15 g (2.8 mmol) of sodium dithiolate and 0.31 g (2.8 mmol) of dichloroacetonitrile in 15 mL of dry DMF was reacted at room temperature for 16 hours. The reaction mixture was filtered to give 0.33 g of the title compound as a dark brown powder which melted at 165°–167° C. (dec) in a yield of 50 percent of theoretical. MS (EI) m/z 235 (M$^+$), 205, 192, 160, 149, 129, $C_3HNS_5$ requires 235.

EXAMPLE IV 5,5-Di(aminocarboxyl)-1,3-Dithiolo(4,5-d)-1,3-dithiole-2-thione

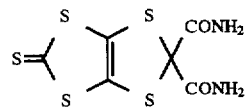

A reaction mixture of 1.15 g (2.8 mmol) of sodium dithiolate and 0.73 g (2.8 mmol) of 2,2-dibromomalonamide in 15 mL of dry DMF was reacted at room temperature for 4 hours. The reaction mixture was filtered to give 0.42 g of the title compound as a yellow-brown powder which melted at 186°–188° C. (dec) in a yield of 58 percent of theoretical. $^1$H NMR (DMSO-$d_6$) δ7.89, 7.87 (2H each, s, NH); $^{13}$C NMR (DMSO-d6) δ213.82, 165.85, 124.05, 80.61. Upon analysis, the product was found to have carbon, hydrogen and nitrogen contents of 24.87, 1.36 and 8.67 percent respectively, as compared with the theoretical contents of 24.31, 1.36 and 9.45 percent, respectively, as calculated for $C_6H_4N_2O_2S_5$, required for the above-named structure.

Preparation of Starting Materials

The bis(tetraethylammonium)bis-(2-thioxo-1,3-dithiole-4,5-dithiolate) Zn(II) corresponding to the formula:

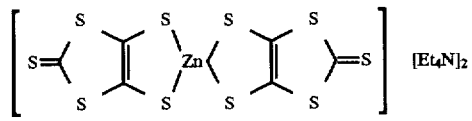

and employed as a starting material is a known compound. The compound and its preparation are found in Hansen et al., *J. Chem. Soc. Perkins Trasn.* 1, 1991, pages 2873–2875, especially page 2874 and also by Kiki et al. in *J. Chem. Soc. Chem. Commun.*, 1987, pages 335–336.

The 4,5-dimercapto-1,3-dithiole-2-thione alkali metal salt corresponding to the formula

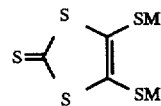

wherein M represents cesium, lithium, potassium or sodium and employed as starting materials are well known compounds and can be prepared as taught in the literature.

The di- and trihaloalkyl reactants employed as starting materials are well known compounds and can either be obtained commercially or prepared as taught in the literature.

The 2,2-dihalomalonamide employed as starting materials are well known compounds and can either be obtained commercially or prepared as taught in the literature.

Antimicrobial Activity

The compounds of this invention are useful as antimicrobial additives, and they can be added to industrial products such as paints, inks, adhesives, soaps, cutting oils, textiles, and paper and pigment slurries and to styrene-butadiene latexes used for paper coatings.

The compounds are also useful as antimicrobial additives in such personal care products as hand creams, lotions, shampoos, and hand soaps. A further advantage of this invention is its cost-effectiveness for applications which need to have an antimicrobial continuously replenished, such as in cooling towers and pulp and paper mills.

As appreciated in the art, not all of the compounds disclosed herein are active at the same concentrations or against the same microbial species. That is, there is some compound-to-compound variation in antimicrobial potency and spectrum of antimicrobial activity.

The present invention is also directed to a method for inhibiting microorganisms which comprises contacting said microorganisms or habitat thereof with a composition containing an antimicrobially effective amount of at least one of the compounds of this invention set forth hereinabove of Formula 1b or 1c.

The antimicrobial compounds of this invention may be added directly to aqueous formulations susceptible to microbial growth, either undiluted or dissolved in inert diluents such as organic solvents such as glycols, alcohols, or acetone. They may also be added alone or in combination with other preservatives.

As used herein, the term "microorganism" is meant to refer to bacteria, fungi, viruses, algae, subviral agents and protozoa.

As used herein, the term "antimicrobially-effective amount" refers to that amount of one or a mixture of two or more of the compounds, or of a composition comprising such compound or compounds, of this invention needed to exhibit inhibition of selected microorganisms. Typically, this amount varies from providing about 1 part per million (ppm) to about 5,000 ppm by weight of the compound to a microbial habitat being contacted with the compound. Such amounts vary depending upon the particular compound tested and microorganism treated. Also, the exact concentration of the compounds to be added in the treatment of industrial and consumer formulations may vary within a product type depending upon the components of the formulation. A preferred effective amount of the compound is from about 1 ppm to about 500 ppm, more preferably from about 1 ppm to about 50 ppm by weight, of a microbial habitat.

The term "microbial habitat" refers to a place or type of site where a microorganism naturally or normally lives or grows. Typically, such a microbial habitat will be an area that comprises a moisture, nutrient, and/or an oxygen source such as, for example, a cooling water tower or an air washing system.

The terms "inhibition", "inhibit" or "inhibiting" refer to the suppression, stasis, kill, or any other interference with the normal life processes of microorganisms that is adverse to such microorganisms, so as to destroy or irreversibly inactivate existing microorganisms and/or prevent or control their future growth and reproduction.

The antimicrobial activity of the compounds of the present invention is demonstrated by the following techniques.

The antimicrobial activity of the compounds of the present invention is set forth as the minimum inhibitory concentration (MIC) for the active compounds and is determined for nine (9) bacteria, using nutrient agar, and seven (7) yeast and fungi, using malt yeast agar. This determination is conducted using a one percent solution of the test compound prepared in a mixture of acetone and water.

Nutrient agar is prepared at pH 6.8, representing a neutral medium, and at pH 8.2, representing an alkaline medium. The nutrient agars are prepared by adding 23 g of nutrient agar to one-liter of deionized water. In addition, the alkaline medium is prepared by adjusting a 0.04M solution of N-[tris-(hydroxymethyl)methyl]-glycine buffered deionized water with concentrated sodium hydroxide to a pH of 8.5.

Malt yeast agar is prepared by adding 3 g yeast extract and 45 g malt agar per liter of deionized water. The specific agar is dispensed in 30 mL aliquots into 25×200 mm test tubes, capped and autoclaved for 15 minutes at 115° C.

The test tubes containing the agar are cooled in a water bath until the temperature of the agar is 48° C. Then, an appropriate amount of the one percent solution of the test compound is added (except in the controls where no compound is added) to the respective test tubes so that the final concentrations are 500, 250, 100, 50, 25, 10, 5, 2.5, 1.0 and zero parts per million of the test compound in the agar, thus having a known concentration of test compound dispersed therein. The contents of the test tubes are then transferred to respective petri plates. After drying for 24 hours, the petri plates containing nutrient agar are inoculated with bacteria and those containing malt yeast agar are inoculated with yeast and fungi.

The inoculation with bacteria is accomplished by using the following procedure. Twenty-four hour-cultures of each of the bacteria are prepared by incubating the respective bacteria in tubes containing nutrient broth for 24 hours at 30° C. in a shaker. Dilutions of each of the 24 hour-cultures are made so that nine separate suspensions (one for each of the nine test bacteria) are made, each containing $10^8$ colony forming units (CFU) per mL of suspension of a particular bacteria. Aliquots of 0.3 mL of each of the bacterial suspensions are used to fill the individual wells of Steer's Replicator. For each microbial suspension, 0.3 mL was used to fill three wells (i.e., three wells of 0.3 mL each) so that for the nine different bacteria, 27 wells are filled. The Steer's Replicator is then used to inoculate both the neutral and alkaline pH nutrient agar petri plates.

The inoculated petri plates are incubated at 30° C. for 48 hours and then read to determine if the test compound which is incorporated into the agar prevented growth of the respective bacteria.

The inoculation with the yeast and fungi is accomplished as follows. Cultures of yeast and fungi are incubated for seven days on malt yeast agar at 30° C. These cultures are used to prepare suspensions by the following procedure. A suspension of each organism is prepared by adding 10 mL of sterile saline and 10 microliters of octylphenoxy polyethoxy ethanol to the agar slant of yeast or fungi. The sterile saline/octylphenoxy polyethoxy ethanol solution is then agitated with a sterile swab to suspend the microorganism grown on the slant. Each resulting suspension is diluted into sterile saline (1 part suspension to 9 parts sterile saline). Aliquots of these dilutions are placed in individual wells of Steer's Replicator and petri plates inoculated as previously described. The petri plates are incubated at 30° C. and read after 48 hours for yeast and 72 hours for fungi.

Table I lists the bacteria, yeast and fungi used in the MIC test described above along with their respective American Type Culture Collection (ATCC) identification numbers.

TABLE I

| Organisms used in the Minimum Inhibitory Concentration Test | |
|---|---|
| Organism | ATCC No. |
| Bacteria | |
| Bacillus subtilis (Bs) | 8473 |
| Enterobacter aerogenes (Ea) | 13048 |
| Escherichia coli (Ec) | 11229 |
| Klebsiella pneumoniae (Kp) | 8308 |
| Proteus vulgaris (Pv) | 881 |
| Pseudomonas aeruginosa (Pa) | 10145 |
| Pseudomonas aeruginosa (PRD-10) | 15442 |

TABLE I-continued

Organisms used in the Minimum Inhibitory Concentration Test

| Organism | ATCC No. |
|---|---|
| Salmonella choleraesuis (Sc) | 10708 |
| Staphylococcus aureus (Sa) | 6538 |
| Yeast/Fungi | |
| Aspergillus niger (An) | 16404 |
| Candida albicans (Ca) | 10231 |
| Penicillium chrysogenum (Pc) | 9480 |
| Saccharomyces cerevisiae (Sc) | 4105 |
| Trichoderma viride (Tv) | 8678 |
| Aureobasidium pullulan (Ap) | 16622 |
| Fusarium oxysporum (Fo) | 48112 |

In Tables II and III, the MIC values of the compounds of the present invention as compared to the MIC of a standard commercial preservative (with 1-(3-chloroallyl)-3,5,7-triaza-1-azoniaadamantane chloride as the active agent, and referred to in Tables II and III as "STANDARD") are set forth for the bacteria organisms and yeast/fungi organisms which are listed in Table I.

TABLE II

Minimum Inhibitory Concentrations for Test Compounds in Bacteria Species (in ppm)

| Compound (Example No.) | | Bs | Ea | Ec | Kp | Pv | PRD | Pa | Sc | Sa |
|---|---|---|---|---|---|---|---|---|---|---|
| STANDARD | pH 6.8 | <10 | 100 | 50 | 25 | 50 | >500 | >500 | 50 | 25 |
| | pH 8.2 | 250 | 500 | >500 | 500 | 500 | >500 | >500 | >500 | 500 |
| (I) | pH 6.8 | >500 | >500 | >500 | >500 | >500 | >500 | >500 | >500 | >500 |
| | pH 8.2 | >500 | >500 | >500 | >500 | >500 | >500 | >500 | >500 | >500 |
| (II) | pH 6.8 | >500 | >500 | >500 | >500 | >500 | >500 | >500 | >500 | >500 |
| | pH 8.2 | >500 | >500 | >500 | >500 | >500 | >500 | >500 | >500 | >500 |
| (III) | pH 6.8 | >500 | >500 | >500 | >500 | >500 | >500 | >500 | >500 | >500 |
| | pH 8.2 | >500 | >500 | >500 | >500 | >500 | >500 | >500 | >500 | >500 |
| (IV) | pH 6.8 | 25 | >500 | 250 | 500 | 100 | >500 | >500 | >500 | 50 |
| | pH 8.2 | 250 | >500 | >500 | >500 | >500 | >500 | >500 | >500 | >500 |

TABLE III

Minimum Inhibitory Concentrations for Test Compounds in Yeast/Fungi Species (in ppm)

| COMPOUND EXAMPLE NO. | An | Ca | Pc | Sc | Tv | Ap | Fo |
|---|---|---|---|---|---|---|---|
| STANDARD | >500 | >500 | >500 | 500 | >500 | >500 | >500 |
| I | <10 | <10 | <10 | >500 | >500 | <10 | >500 |
| II | >500 | >500 | >500 | >500 | >500 | >500 | >500 |
| III | 250 | 500 | 250 | 250 | 500 | 50 | 250 |
| IV | 100 | 500 | 250 | 250 | 500 | 25 | 250 |

Marine Antifouling Activity

The present invention is also directed to a method for inhibiting marine organisms. The term "marine organisms" is meant to include marine animals, such as barnacles, serpulid, bryozoa, oysters and hydroids, and marine plants, such as green algae and brown algae. The method for inhibiting marine organisms comprises contacting a surface exposed to a marine environment in which marine organisms grow with a marine antifouling effective amount of the compound of this invention.

As appreciated by those skilled in the art, not all of the compounds disclosed herein are active at the same concentrations or against the same marine organism species. That is, there may be some compound-to-compound variation in marine antifouling potency and spectrum of marine antifouling activity. Furthermore, the level of a specific compound's marine antifouling activity may be dependent on various factors including the specific materials with which the compound is formulated.

As used herein, the term "marine antifouling effective amount" refers to that amount of one or a mixture of two or more of the compounds of this invention needed to exhibit inhibition of selected marine organisms. Typically, this amount varies from providing about 1 weight percent to about 30 weight percent of the compound to a marine antifouling composition which is used to treat a surface exposed to a marine environment in which marine organisms live or grow. Such amounts vary depending upon the particular compound tested and marine organism to be treated. Also, the exact concentration of the compounds to be added in the preparation of industrial and consumer formulations may vary within a product type depending upon the components of the formulation.

A composition comprising a marine antifouling effective amount of the compound will also comprise an inert diluent which may be, for example, in the form of a paint. Particularly preferred are those paints having a vinyl resin binder such as, for example, a plasticized polyvinyl chloride or a polyvinyl chloride-polyvinyl acetate type. Preferably, the binders are formulated as latexes or emulsions. In a paint composition, the compound of the present invention is preferably used in an amount from about 1 to about 30 weight percent and, most preferably, from about 10 to about 25 weight percent. In addition to vinyl resin binder paints, epoxy and polyurethane binder paints containing the compound may also be useful. Coatings and films prepared from paints comprising the compound of the present invention typically remain substantially free from build-up of marine organisms for periods ranging from about 3 to about 12 months, depending upon the concentration of the compound and the thickness of the applied coating or film.

The term "a surface exposed to a marine environment" refers to a surface where a marine organism naturally or normally lives or grows. Typically, such a surface will be an area that is in continual or periodic contact with a marine environment such as an ocean or other body of water. Typical surfaces include, for example, a ship hull.

What is claimed is:

1. A 1,3-dithiolo(4,5-d)-1,3-dithiino-2-thione compound corresponding to the formula:

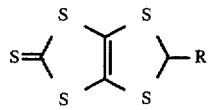

wherein R represents —Br, —Cl, —F, or —CN.

2. The compound of claim 1 which is 5-chloro-1,3-dithiolo(4,5-d)-1,3-dithiole-2-thione.

3. The compound of claim 1 which is 5-cyano-1,3-dithiolo(4,5-d)-1,3-dithiole-2-thione.

4. An antimicrobial composition comprising an inert diluent and an antimicrobially-effective amount of a 1,3-dithiolo(4,5-d)-1,3-dithiino-2-thione compound corresponding to the formula:

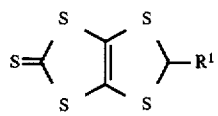

wherein $R^1$ represents —Br, —Cl, —F, —CN or —CH$_2$(CH$_2$)$_n$CH$_3$ and n is an integer of from 0 to 10.

5. The composition of claim 4 wherein the compound is 5-chloro-1,3-dithiolo(4,5-d)-1,3-dithiole-2-thione.

6. The composition of claim 4 wherein the compound is 5-cyano-1,3-dithiolo(4,5-d)-1,3-dithiole-2-thione.

7. A method for inhibiting microorganisms in a microbial habitat comprising contacting said microbial habitat with a composition containing an inert diluent and an antimicrobially-effective amount of an active material which is a 1,3-dithiolo(4,5-d)-1,3-dithiino-2-thione compound corresponding to the formula:

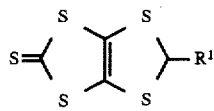

wherein $R^1$ represents —H, —Br, —Cl, —F, —CN or —CH$_2$(CH$_2$)$_n$CH$_3$ and n is an integer of from 0 to 10.

8. The method of claim 7 wherein the compound is 1,3-dithiolo(4,5-d)-1,3-dithiole-2-thione.

9. The method of claim 7 wherein the compound is 5-chloro-1,3-dithiolo(4,5-d)-1,3-dithiole-2-thione.

10. The method of claim 7 wherein the compound is 5-cyano-1,3-dithiolo(4,5-d)-1,3-dithiole-2-thione.

11. The method of claim 7 wherein the compound is present in the composition in an amount to provide from about 1 part per million to about 5,000 parts per million by weight of the compound to the microbial habitat.

12. A composition useful in preventing the growth of marine organisms on a surface exposed to a marine environment in which marine organisms grow comprising an inert diluent and a marine antifouling effective amount of a 1,3-dithiolo(4,5-d)-1,3-dithiino-2-thione compounds corresponding to the formula:

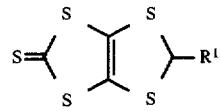

wherein $R^1$ represents —Br, —Cl, —F, —CN or —CH$_2$(CH$_2$)$_n$CH$_3$ and n is an integer of from 0 to 10.

13. The composition of claim 12 wherein the compound is 5-chloro-1,3-dithiolo(4,5-d)-1,3-dithiole-2-thione.

14. The composition of claim 12 wherein the compound is 5-cyano-1,3-dithiolo(4,5-d)-1,3-dithiole-2-thione.

15. A method for preventing the growth of marine organisms on a surface exposed to a marine environment in which marine organisms grow comprising contacting said surface with a composition containing an inert diluent and a marine antifouling effective amount of an active material which is a 1,3-dithiolo(4,5-d)-1,3-dithiino-2-thione compound corresponding to one of the formulae:

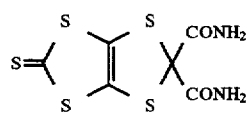

or

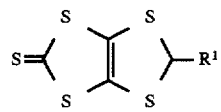

wherein $R^1$ represents —H, —Br, —Cl, —F, —CN or —CH$_2$(CH$_2$)$_n$CH$_3$ and n is an integer of from 0 to 10.

16. The method of claim 15 wherein the compound is 1,3-dithiolo(4,5-d)-1,3-dithiole-2-thione.

17. The method of claim 15 wherein the compound is 5-chloro-1,3-dithiolo(4,5-d)-1,3-dithiole-2-thione.

18. The method of claim 15 wherein the compound is 5-cyano-1,3-dithiolo(4,5-d)-1,3-dithiole-2-thione.

19. The method of claim 15 wherein the compound is 5,5-di(aminocarboxyl)-1,3-dithiolo(4,5-d)-1,3-dithiole-2-thione.

20. The method of claim 15 wherein the composition comprises from about 1 to about 30 weight percent of the 1,3-dithiolo(4,5-d)-1,3-dithiole-2-thione compound.

* * * * *